United States Patent [19]

Rosaen

[11] Patent Number: 4,928,515
[45] Date of Patent: May 29, 1990

[54] OIL MIST SENSOR

[76] Inventor: Nils O. Rosaen, P.O. Box 242, Clarkston, Mich. 48016

[21] Appl. No.: 277,869

[22] Filed: Nov. 30, 1988

[51] Int. Cl.⁵ ............................................. B01D 17/02
[52] U.S. Cl. ...................................... 73/61 R; 55/462
[58] Field of Search ............ 55/462; 73/61 R, 61.1 R, 73/64, 53, 863.21, 863.22, 19

[56] References Cited

U.S. PATENT DOCUMENTS

| | | | |
|---|---|---|---|
| 3,345,807 | 10/1967 | Van Felden | 55/462 |
| 3,698,159 | 10/1972 | Ruse | 55/462 |
| 4,056,371 | 11/1977 | Diemer, Jr. et al. | 55/462 |
| 4,395,902 | 8/1983 | Espenscheid et al. | 73/61 R |
| 4,678,488 | 7/1987 | Howard et al. | 73/863.21 |
| 4,699,886 | 10/1987 | Lelong | 73/663.21 |

FOREIGN PATENT DOCUMENTS

| | | | |
|---|---|---|---|
| 731991 | 5/1980 | U.S.S.R. | 55/462 |
| 2081896 | 2/1982 | United Kingdom | 73/19 |

*Primary Examiner*—Hezron E. Williams
*Attorney, Agent, or Firm*—Gifford, Groh, Sprinkle, Patmore and Anderson

[57] ABSTRACT

An air-oil mist sensor includes a collecting plate disposed immediately downstream from a plurality of narrow bores. Oil separates from the mist and deposits on the collecting plate. Thereafter, the separated oil is led to a reservoir where it is collected and stored during a collection cycle. At the beginning of a sampling cycle, a piston is moved into the reservoir to pressurize any oil contained therein. The force of the piston is transferred by the oil to a second, orthogonal piston which is used to actuate a switch mechanism and provide an indication whether oil is present. As the second piston is displaced, an opening is uncovered to drain oil from the reservoir. In the event that the reservoir contains air due to the collection of an insufficient amount of oil, the air is simply compressed by the piston and force is not transferred to the second piston to actuate the switch. About 98% of the oil in the mist is stripped from it by passage through the sensor.

21 Claims, 2 Drawing Sheets

OIL MIST SENSOR

BACKGROUND OF THE INVENTION

I. Field of the Invention

This invention relates to a sensing device and, in particular, to a sensing device for the detection of oil in an air-oil or gas-oil lubricating mist.

II. Description of the Prior Art

Lubrication of various machine parts has been achieved in the past by spraying such parts with an oil mist. Such parts, typically bearings, require a constant supply of small quantities of oil to provide the lubricating film necessary to function smoothly and properly. If the system fails to supply sufficient quantity of oil in the oil mist, the bearings begin to wear excessively, causing significant down time and extensive repair costs.

Heretofore it has been difficult to ensure that bearings or other parts are receiving a sufficient quantity of oil from an air-oil mist. Devices for detecting the quantity of oil in an oil mist have previously been known, but due to their sensitivity they have been extremely expensive and unreliable, essentially impractical for most operations.

SUMMARY OF THE PRESENT INVENTION

These and other disadvantages are overcome by the present invention which provides an oil-mist sensor which is both efficient and reasonably priced. The oil-mist sensor of the present invention receives a diverted and relatively small portion of an air-oil mixture and separates the oil from the air on a collecting plate. The collecting plate is disposed directly downstream from a radial wall having holes bored axially therethrough. As the oil mist passes through these bores, the velocity of the air increases, thus stripping the oil from the air and onto the collecting plate.

Downstream from the collecting plate the separated oil is collected in a reservoir, during a collecting cycle, while the air is vented to the atmosphere by an outlet. Upon receipt of a timing signal, the reservoir is sampled for the presence of oil. Preferably, this is accomplished by means of a cylinder piston which is forced into the reservoir applying pressure to the oil contained there. Since the oil is incompressible, the pressure is translated to a second, orthogonal actuator piston which then engages a switch mechanism to indicate the presence of oil. As the actuator piston is displaced, an opening is uncovered through which the collected oil can returns to the outlet.

In the event that the oil mist contains an insufficient amount of oil, little or no oil will collect in the reservoir and, upon actuation, the piston will compress only the air contained there. The compression of only air, however, is insufficient to move the actuator piston. The switch mechanism therefore fails to indicate the presence of oil and the operator is alerted to this fact.

Preferably, the piston cylinder is operable in connection with a source of pressurized air and a valve connected to a conventional timer. Thus, the collecting cycle and the sampling cycle can be precisely controlled.

It is also preferred that the radial wall comprises an insertable spindle or cartridge so that throughbores of varying number and/or sizes can be used to regulate the amount of oil collected during a collecting cycle. Preferably, a sliding valve is mounted to a rotatable shaft for movement with it, positioned to cover the holes through the radial wall. Rotation of the shaft moves the valve so as to vary the number of holes that are covered by the valve, so as to adjust the amount of oil collected over a given collection cycle.

BRIEF DESCRIPTION OF THE DRAWING

The present invention will be more fully understood by reference to the following detailed description when read in conjunction with the accompanying drawing in which like reference characters refer to like parts throughout the several views and in which.

DETAILED DESCRIPTION OF THE PREFERRED EMBODIMENT

Figure 1:
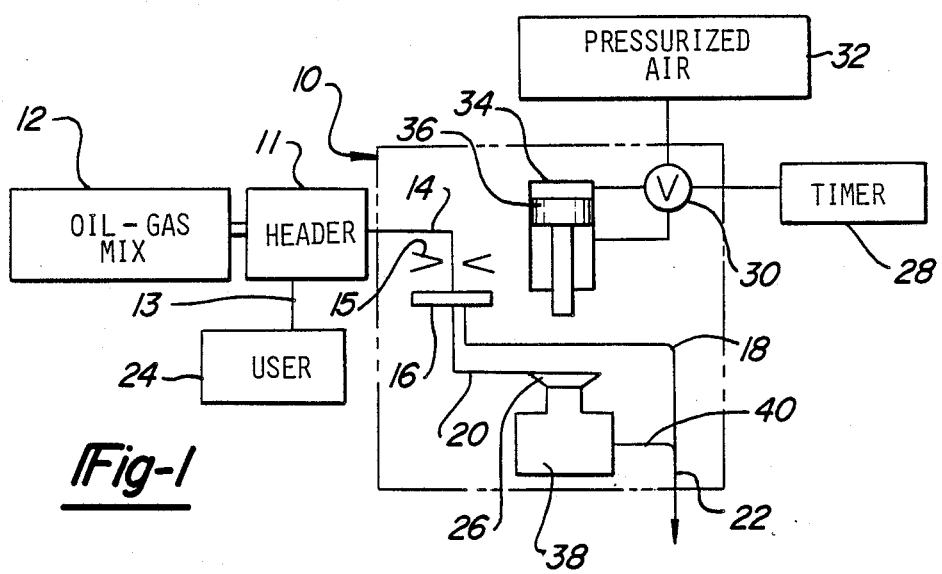
FIG. 1 is a schematic representation of the oil-mist sensor of the present invention.

Referring first to FIG. 1, a sensing device 10 is thereshown in schematic form receiving a small amount of an air-oil mixture from a conventional low-pressure source 12 diverted at a conventional header 11 to an inlet 14 of the device 10. The major portion of the air-oil mixture is delivered through the head 11 and an associated line 13 to a user location 24, for example, a bearing. The small diverted portion of air-oil mixture flows through a fluid passageway past a restricted portion 15 and deposits on a collecting plate 16. The restricted portion 15 and the collecting plate 16 together substantially separate the oil from the air-oil mixture to yield an airflow (designated at 18) separate from an oilflow (designated at 20). The airflow 18 from which the oil has been separated is vented through an outlet 22 to, for example, the atmosphere. Although an air-oil mist is described, it will be understood that any oil-gas mixture can be used as an oil mist, particularly in systems sensitive to air.

The oil which is separated from the diverted portion of the air-oil mixture is collected in a reservoir 26 during a collecting cycle. At a time prescribed by a timer 28, a valve 30 connects a source of compressed air 32 to the upper portion of a cylinder 34 to drive a piston 36 downwardly into the reservoir 26. The oil collected in the reservoir 26, being essentially incompressible, fluidly and/or mechanically actuates a switch 38 to indicate the presence of oil in the reservoir, specifically, the oil which has been separated or "stripped" from the diverted portion of air-oil mixture.

Following operation of the switch 38, oil is drained from the reservoir 26, for example, to the outlet 22, by means of a bypass port or drain passageway 40. At the conclusion of the sampling cycle, which may also be indicated by the timer 28, the valve 30 directs compressed air to the bottom portion of the cylinder 34 to raise the piston 36 out of the reservoir 26 to begin another collecting cycle. The switch 38 is then reset, either mechanically (for example, by spring biasing) or pneumatically, as is convenient.

Figure 2:
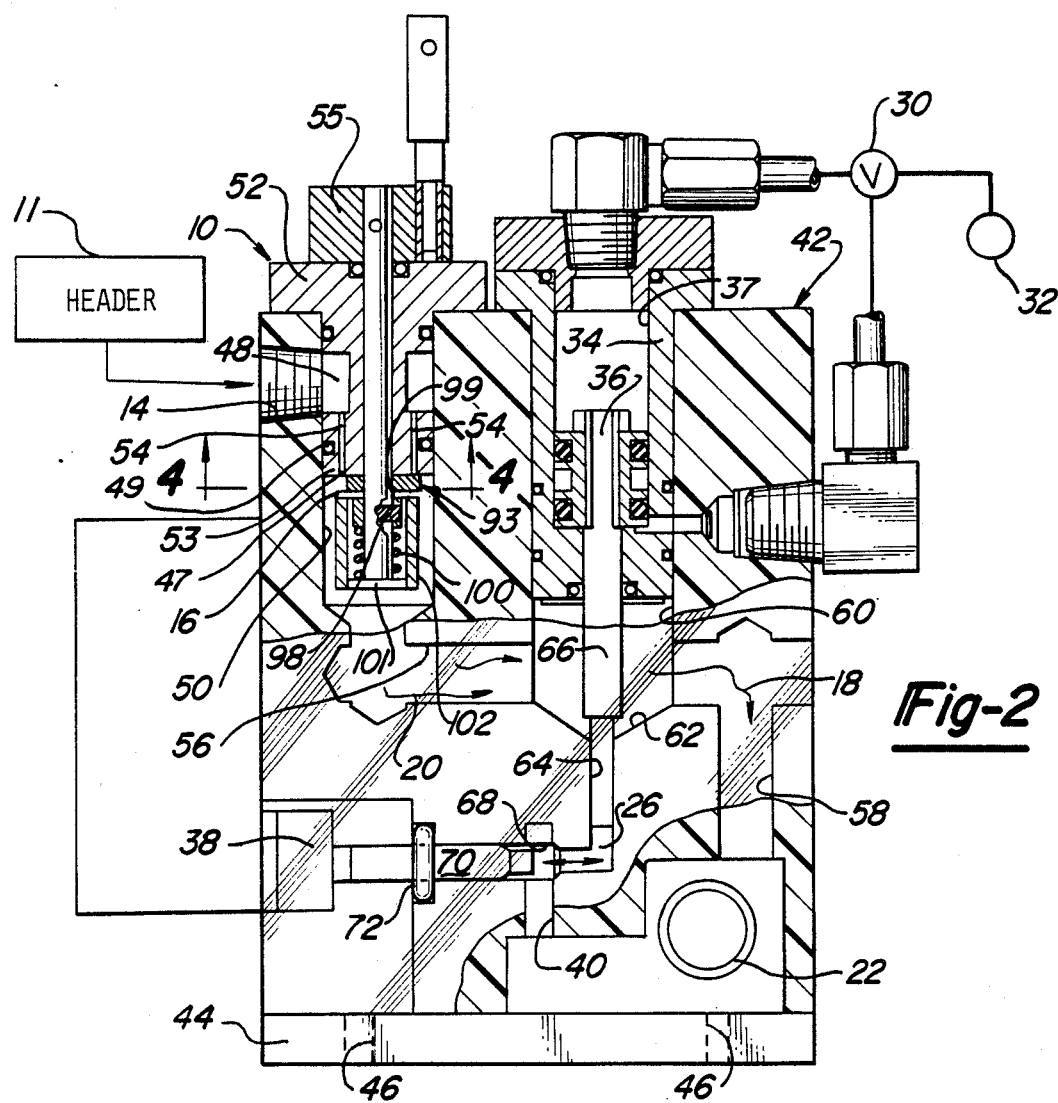
FIG. 2 is a partially cross-sectioned front view of the preferred embodiment.
Figure 3:
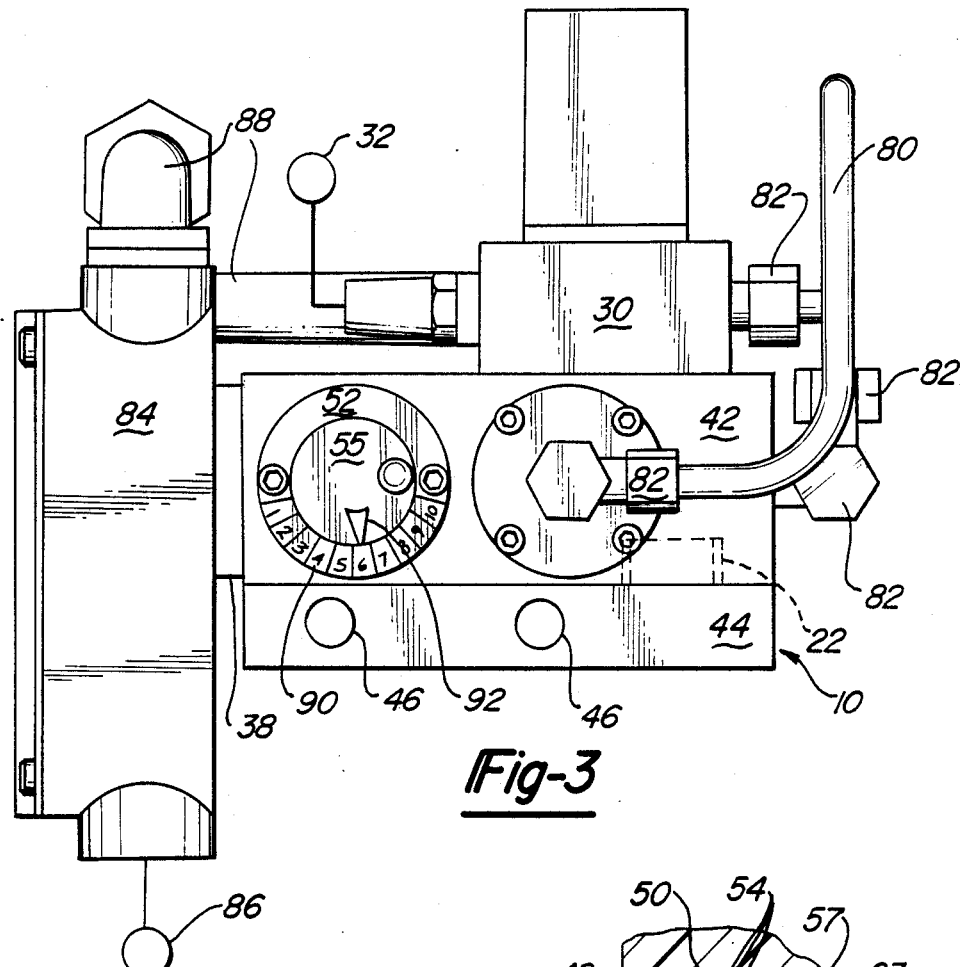
FIG. 3 is a top view of the preferred embodiment.
Figure 5:
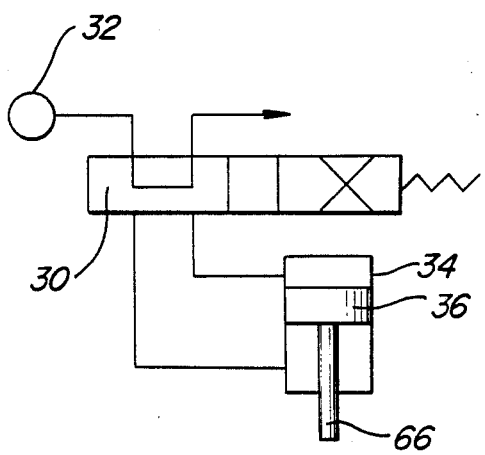
FIG. 5 is a schematic representation of the compressed air valve.

Referring now to FIGS. 2 and 3, a preferred embodiment of the device 10 is thereshown comprising a housing 42 mounted to a base 44 having mounting holes 46 bored therethrough. While the housing 42 can be made of aluminum or any other similar metal, preferably it is made of a transparent, oil-resistant plastic. This enables an operator visually to observe the collection of oil in the reservoir 26 in addition to the electronically-timed sampling and indicating performed by the device 10.

The inlet 14 opens to a cylindrical bore 50 formed in the housing 42. A cylindrical spindle 52 is inserted into the bore 50 and includes a centrally situated annular portion 51 of reduced diameter. The bore 50 and portion 51 together define an annular chamber 48 in the bore 50. The reduced diameter portion 51 also defines a radial wall 53 spanning the bore 50 and extending from the annular chamber 48 to the bottom of the spindle 52. One or more small diameter axial throughbores 54 extend through the wall 53 connecting the annular chamber 48 to the bottom of the bore 50. The restricted portion 15 of the fluid passageway 47 thus comprises the axial throughbores 54.

A plurality of seals such as O rings 49 or the like are positioned between the spindle 52 and the housing 42 so as to seal the bore 50 above and below the annular chamber 48. The air-oil mixture entering the annular chamber 48 passes through the axial bores 54 into the bottom portion of the bore 50. As the mixture passes through the small diameter of the axial bores 54 its velocity increases in the well known manner, thus stripping substantially all of the oil from the air-oil mixture by impingement upon the flat, annular collecting plate 16. The stripped oil then flows to the bottom of the bore 50. The small diameter axial throughbores 54 serve not only to increase the speed of the mist as it impinges upon the plate 16, but also limit the amount of air-oil mist flow through the device 10, and separate the mist flow into a parallel set of smaller flows. The efficiency of separation is thereby made very high, typically on the order of a 98% removal of oil from the mist.

Figure 4:
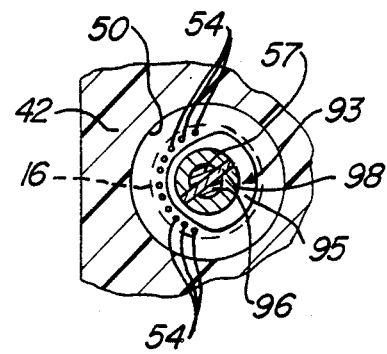
FIG. 4 is a cross-sectional view taken substantially along the line 4—4 in FIG. 2.
Figure 6:
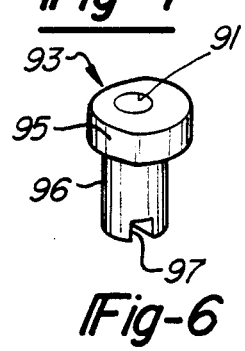
FIG. 6 is a perspective view of a portion of the preferred embodiment of the present invention.

Referring particularly now to FIGS. 2 and 4, the spindle 52 also includes a central axial throughbore through which shaft 57 extends. The top of the shaft 57 extends through the top of the spindle 52 and the housing 42 and is capped by a knob 55 which rotates the shaft 57 in the bore. The bottom end of the shaft 57 extends below the radial wall 53. The shaft 57 passes through a bore 91 in a sliding valve 93. The valve 93 includes a valve head 95 adapted to cover and close the ends of some or all of the bores 54, the number of bores 54 closed being dependent upon the rotational position of the valve 93. The valve 93 also includes a valve stem 96 having a transverse slot 97 formed therein. A pin 98 is located in the slot 97 and engages the shaft 57 so as to key movement of the valve 93 (and closing of the bores 54 by the valve head 95) to rotation of the shaft 57. The valve 93 is more clearly shown in FIG. 6.

The flat annular collecting plate 16 includes a central hole 99 through which the valve stem 96 and the shaft 57 pass. A spring 100 is retained beneath the collecting plate 16 by a screw 101 and biases the valve 93 against the ends of the bores 54 so as to minimize leakage. A sleeve 102 can optionally cover the spring 100. The plate 16 thus speeds separation of the oil from the mist by the bores 54. If the plate 16 was not present the spring 100 and the head of the screw 101 would instead collect the oil, and it would take longer for the oil to reach the second bore 56, decreasing the reliability of the device 10. The use of the spring 100 and screw 101 as an oil collector is of course within the scope of the present invention, however.

As best shown in FIG. 2, the second bore 56 is formed transversely in the housing 42 so as to be continuous with the bottom of the bore 50. A third bore 58 connects the opposite end of the transverse bore 56 to the outlet 22. The bores 50, 56 and 58 comprise a fluid passageway extending from the inlet 14 to the outlet 22 in a generally S-shaped configuration. This fluid passageway transmits the air resulting after separation of the oil from the air-oil mist to the outlet 22. A fourth bore 60 is formed in the housing 42 roughly parallel to the bore 50 and intersecting the middle of the transverse bore 56 at substantially a right angle. At its bottom end the fourth bore 60 leads to a generally conical depression 62 which terminates in a second fluid passageway 64 coaxial with, but narrower than, the fourth bore 60. The cylinder 34 is inserted into the fourth bore 60 and is sealed therein with O rings or the like. Preferably, the cylinder 34 is pneumatically operated in the conventional fashion, having the piston 36 dividing an internal chamber 37 into upper and lower portions each of which includes a port connected to a valve 30 for the delivery of pressurized air from a source 32.

A rod 66 is attached to the piston 36 and is movable with it between an upper and a lower position. In its lower position, shown in FIG. 2, the rod 66 extends through the fourth bore 60 and into the coaxial second fluid passageway 64. In its upper position (not shown) the rod 66 is retracted from the second fluid passageway 64 and is contained within the fourth bore 60 and the second bore 56.

The lower end of the second passageway 64 connects to a third fluid passageway 68 at right angles thereto. A piston 70 is slidably disposed in the third fluid passageway 68 and is operatively connected to the switch mechanism 38. The switch 38 may be any type known in the art which can be actuated by linear movement. A seal member 72 is disposed between the switch mechanism 38 and the fluid in the third fluid passageway 68. As the piston 70 is slid to its actuating position, a drain passageway 40 is opened to the third fluid passageway 68 to drain the oil from this area once the switch mechanism 38 is actuated. The switch mechanism can include return means (not shown) for returning the piston 70 to its initial position (to the far right, as viewed in FIG. 2), or the piston 70 can be biased by a spring or the like for the same purpose.

Referring particularly now to FIG. 3, the valve 30 is shown located between the source of pressurized air 32 and various conduits 80 and fittings 82 connecting the outlets of the valve 30 to the ports of the cylinder 34. Also including in the device 10 is a receptacle box 84 adapted to be connected to a standard power source 86. A conduit 88 leads appropriate connecting wires to the valve 30. Finally, the top surface of the spindle 52 includes a scale 90 graduated arbitrarily from 1 to 10. An indexing arrow 92 is located on the adjusting knob 55 which can be rotated to select a given setting, varying the position of the sliding valve 57.

In operation, 98% or more of the oil in the air-oil mixture is stripped from the mist by the collection plate 16 and drops to the bottom of the bore 50 and into the second bore 56 along the path generally indicated by the arrow 20. The oil then collects in the reservoir 26 formed by the depression 62. Because the piston rod 66 is normally in a raised position, oil then collects in the bottom of the second fluid passageway 64. The mechanical resistance of switch mechanism 38 and the piston 70 is not overcome by this small pressure head. However, upon a timing signal the valve 30 causes the piston 36 to descend to its lower position to "sample" the reservoir for the presence of oil. As the piston rod 66 descends, the essentially incompressible oil in the reservoir 26 forces the piston actuator 70 to actuate the switch mechanism 38, to indicate the presence of oil in the device 10 and thereby in the mist.

As the piston actuator 70 moves, the drain passageway 40 is uncovered to provide for an outlet of the oil contained in the reservoir 26. A second timing signal, or the removal of the first timing signal, operates the valve 30 to restore the piston 36 to its raised position. This, in turn, releases pressure on the piston actuator 70 which then returns to its normal position covering the drain passageway 40. Oil can again begin to collect in the reservoir 26 for the next periodic sampling.

In the event that the oil-gas mixture contains an insufficient quantity of oil or is devoid of oil, little or no oil will be separated by the collecting plate 16 to be collected in the reservoir 26. Consequently, upon depression of the piston rod 66, insufficient pressure will be developed to move the piston actuator 70 to actuate the switch mechanism 38, thus indicating the absence of oil in the mist. It will be understood by those skilled in the art that the switch mechanism 38 could also be operated in a reverse manner, so that in the event that oil is not detected in the reservoir 26, an alarm or warning is given that insufficient lubrication is being delivered to the user device 24.

Having described the structural and operational features of the invention, its advantages will readily be appreciated. The present invention provides an inexpensive oil mist sensor which can both visually and electronically indicate the presence of a sufficient quantity of oil in an oil mist being used to lubricate moving parts such as bearings. The device is easily connected to the system lines and header, to a power source and to a timer to select the extent of the collecting cycle and the sampling cycle. Moreover, the adjusting knob 55 can be used to vary the effective flow rate of the air-oil mist and thereby further modify the quantity of oil separated from the oil mist. Through experimentation it has been determined that for a unit pressure between 10 and 20 inches of water and a cycle time of two minutes, the adjusting knob should be set at number 5 (the holes 54 about half covered). Conversely, for a cycle time of sixty minutes the knob should be set to number 3 (the holes 54 mostly covered). The best way to determine settings for other cycle times and pressures is simply by trial and error and by visual inspection; enough of the holes 54 should be uncovered to yield (over the desired cycle time) enough oil to permit actuation of the piston 70, but not so much as continued drainage after one cycle interferes with the next cycle.

The foregoing description of the preferred embodiment has been given for clarity of understanding only and no unnecessary limitations should be understood therefrom. Many modifications will be obvious to those skilled in the art to which the invention pertains, without deviation from the spirit of the invention as defined by the scope of the appended claims.

I claim:

1. A device for detecting the presence of oil in an oil-gas mixture, said device comprising:
    a fluid passageway through which said mixture is directed;
    means included in said fluid passageway for separating a quantity of oil from said oil-gas mixture;
    means for collecting said quantity of separated oil in a reservoir for a predetermined collecting cycle;
    means for sampling said reservoir at the end of said collecting cycle to detect the presence of oil;
    means for indicating the presence of oil in said reservoir;
    said separating means comprising means disposed in said fluid passageway for defining at least one restricted portion and a collecting plate disposed in said fluid passageway downstream from said restricted portion;
    said last mentioned means comprising a cylindrical spindle disposed in said fluid passageway and having a downstream and facing said collection plate; and
    wherein said fluid passageway is formed in part by a centrally disposed portion of said spindle having a reduced diameter defining a spindle wall; and wherein said at least one restricted portion comprises at least one bore through said wall, extending from said annular chamber to said downstream end of said spindle.

2. The device as defined in claim 1 wherein said means for separating includes means for varying the cross-sectional area of said restricted portion.

3. The device as defined in claim 1 wherein said means for separating comprises a plurality of said restricted portions and means for closing at least some of said restricted portions.

4. The device as defined in claim 1 wherein said at least one restricted portion includes a plurality of said bores, and wherein said device further comprises a slidable valve positioned between said downstream end of said spindle and said collection plate, said valve abutting against said downstream end of said spindle and located so that sliding movement of said valve results in closing of a variable number of said bores.

5. The device as defined in claim 1 wherein said reservoir for collecting oil comprises a depression in said fluid passageway, said depression leading to a second fluid passageway.

6. The device as defined in claim 5 wherein said second fluid passageway is substantially perpendicular to said fluid passageway at said depression.

7. The device as defined in claim 1 wherein said indicating means is responsive to the detection of the presence of oil by said sampling means.

8. The device as defined in claim 1 wherein said predetermined collection cycle is variable in response to the pressure of said oil-gas mixture.

9. The device as defined in claim 1 further comprising a housing containing at least in part said fluid passageway, said separating means, said collecting means, said sampling means and said indicating means.

10. The device as defined in claim 9 wherein said housing is at least in part transparent.

11. A device for detecting the presence of oil in an oil-gas mixture, said device comprising:
    a fluid passageway through which said mixture is directed;
    means included in said fluid passageway for separating a quantity of oil from said oil-gas mixture;
    means for collecting said quantity of separated oil in a reservoir for a predetermined collecting cycle;
    means for sampling said reservoir at the end of said collecting cycle to detect the presence of oil;
    means for indicating the presence of oil in said reservoir;

said reservoir for collecting oil comprising a depression in said fluid passageway, said depression leading to a second fluid passageway;

said sampling means comprising a rod selectively insertable into said second passageway to apply pressure to a quantity of oil collected therein.

12. The device as defined in claim 11 wherein said means for separating comprises means disposed in said fluid passageway for defining at least one restricted portion and a collecting plate disposed in said fluid passageway downstream from said restricted portion.

13. The device as defined in claim 11 wherein said rod is formed as the end of a piston, said piston being movable between a first position in which said rod is retracted from said second fluid passageway and a second position in which said rod is inserted into said second fluid passageway.

14. The device as defined in claim 13 wherein said piston forms part of a hydraulic cylinder, said cylinder being operated by pressurized air.

15. The device as defined in claim 14 and comprising an electrically controllable valve for directing said pressurized air to operate said cylinder.

16. The device as defined in claim 11 wherein said means for indicating comprises a switch responsive to pressure on said oil in said second fluid passageway.

17. The device as defined in claim 16 wherein said switch comprises a piston actuated switch.

18. The device as defined in claim 16 wherein said second fluid passageway includes a drain passageway to remove said oil from said second fluid passageway after activating said switch.

19. A device for detecting the presence of oil in an oil-gas mixture, said device comprising:
a fluid passageway through which said mixture is directed;
means included in said fluid passageway for separating a quantity of oil from said oil-gas mixture;
means for collecting said quantity of separated oil in a reservoir for a predetermined collecting cycle;
means for sampling said reservoir at the end of said collecting cycle to detect the presence of oil;
means for indicating the presence of oil in said reservoir;
said separating means comprising a plurality of said restricted portions and means for closing at least some of said restricted portions; and
said closing means comprising a sliding valve disposable across said plurality of restricted portions.

20. A device for detecting the presence of oil in an oil-gas mixture, said device comprising:
a fluid passageway through which said mixture is directed;
means included in said fluid passageway for separating a quantity of oil from said oil-gas mixture;
means for collecting said quantity of separated oil in a reservoir for a predetermined collecting cycle;
means for sampling said reservoir at the end of said collecting cycle to detect the presence of oil;
means for indicating the presence of oil in said reservoir; and
said sampling means comprising a rod selectively insertable into said passageway to apply pressure to a quantity of oil collected therein.

21. A device for detecting the presence of oil in an oil-gas mixture, said device comprising:
a fluid passageway through which said mixture is directed;
means included in said fluid passageway for separating a quantity of oil from said oil-gas mixture;
means for collecting said quantity of separated oil in a reservoir for a predetermined collecting cycle;
means for sampling said reservoir at the end of said collecting cycle to detect the presence of oil;
means for indicating the presence of oil in said reservoir; and
said separating means including a sliding valve disposable in said passageway and operable to close off a portion of said passageway.

* * * * *